United States Patent
Reck

(10) Patent No.: US 6,931,930 B2
(45) Date of Patent: Aug. 23, 2005

(54) METHOD FOR DETERMINING THE PRESSURE PRESENT IN THE INTERIOR SPACE OF AN AIR SPRING FOR A MOTOR VEHICLE AND APPARATUS FOR CARRYING OUT THE METHOD

(75) Inventor: Siegfried Reck, Nienburg (DE)

(73) Assignee: ContiTech Luftfedersysteme GmbH, Hannover (DE)

( * ) Notice: Subject to any disclaimer, the term of this patent is extended or adjusted under 35 U.S.C. 154(b) by 0 days.

(21) Appl. No.: 10/273,179

(22) Filed: Oct. 18, 2002

(65) Prior Publication Data

US 2003/0074970 A1 Apr. 24, 2003

(30) Foreign Application Priority Data

Oct. 18, 2001 (DE) .......................................... 101 51 593

(51) Int. Cl.$^7$ .......................... G01N 29/18; G01N 29/20
(52) U.S. Cl. .............................. 73/597; 73/599; 73/629; 73/703
(58) Field of Search ..................... 73/629, 632, 862.59, 73/862.58; 267/64.19

(56) References Cited

U.S. PATENT DOCUMENTS 4,798,369 A * 1/1989 Geno et al. .............. 267/64.11
6,032,535 A * 3/2000 Fischer et al. ................ 73/629
6,073,491 A   6/2000 Fischer et al.

FOREIGN PATENT DOCUMENTS

DE            198 11 982        9/1999

* cited by examiner

*Primary Examiner*—Hezron Williams
*Assistant Examiner*—Nashmiya S. Fayyaz
(74) *Attorney, Agent, or Firm*—Walter Ottesen

(57) ABSTRACT

An ultrasonic pulse/echo measurement arrangement includes an ultrasonic transducer (12), which is mounted spatially fixed on an air spring cover plate (4). The arrangement further includes a fixedly mounted reference reflector (14), a target reflector (16) mounted on a roll-off piston (8) or on the bumper (18) as well as a transmitter/receiver evaluation electronic circuit (30). The running time as well as the amplitude of the reference signal is evaluated to precisely determine the pressure present in the interior space of the air spring. The ultrasonic transducer (12) has a $\lambda/4$-adaptation layer (22), whose impedance does not correspond to the geometric mean of the impedances of the ultrasonic transducer (12) and the ambient air of the interior space (20) of the air spring, but rather, is a mismatch. The evaluation electronic circuit (30) can be calibrated at ambient pressure for the determination of the inner pressure of the air spring. Preferably, the pressure measuring method according to the invention is also used to determine the running-time dependent spring height in an air spring (2) of a motor vehicle.

7 Claims, 4 Drawing Sheets

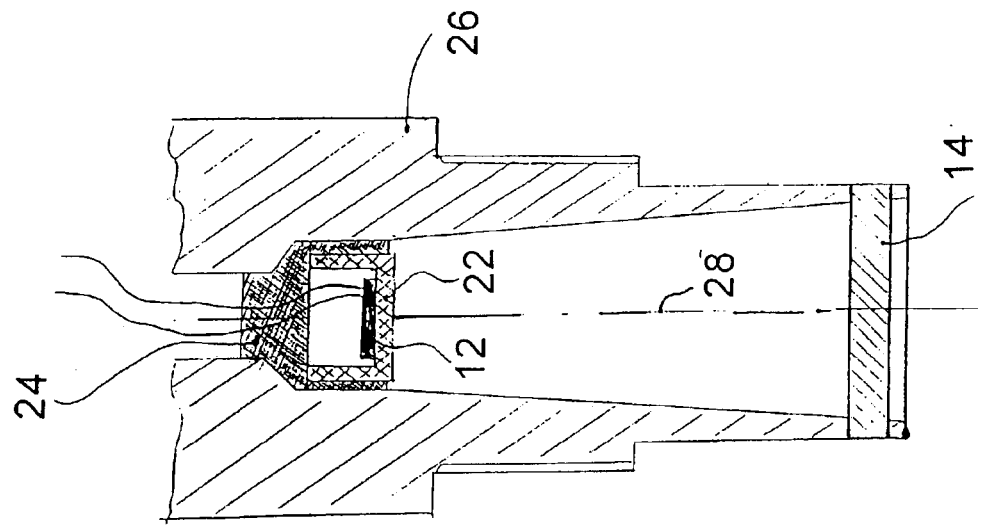
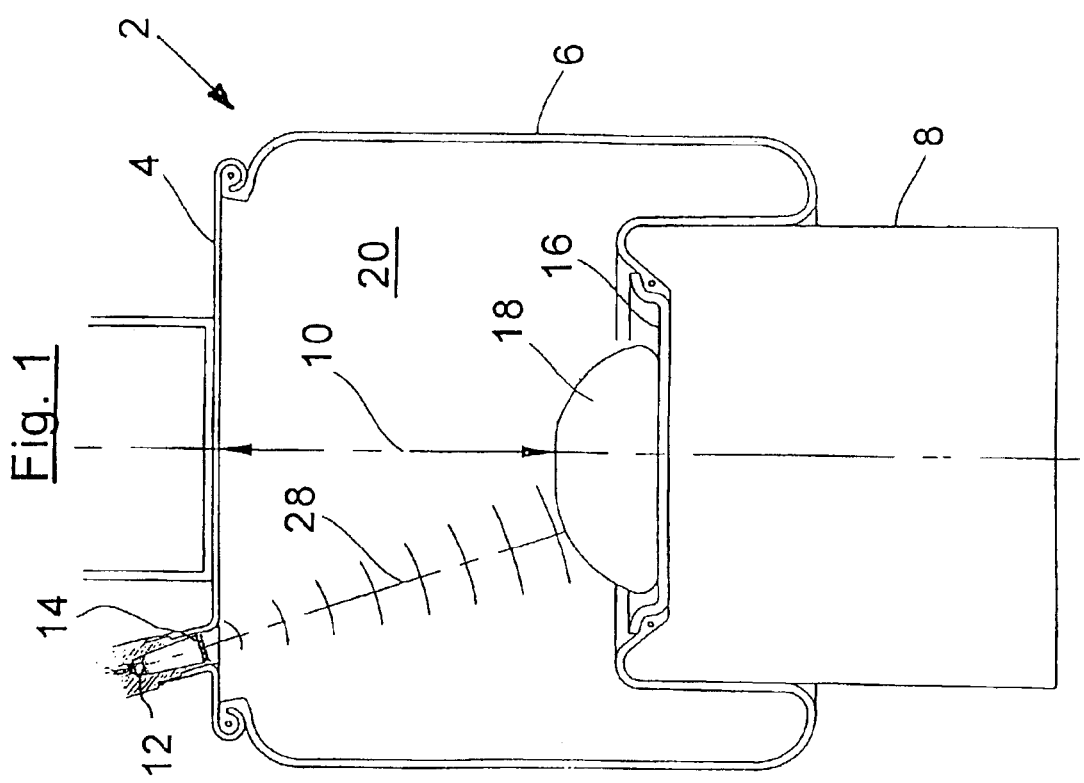

METHOD FOR DETERMINING THE PRESSURE PRESENT IN THE INTERIOR SPACE OF AN AIR SPRING FOR A MOTOR VEHICLE AND APPARATUS FOR CARRYING OUT THE METHOD

FIELD OF THE INVENTION

The invention relates to an ultrasonic method for measuring pressure in an air spring and the use of the measuring result to make corrections in a distance measuring method. Furthermore, the invention relates to an arrangement for carrying out the method. The arrangement includes a piezoceramic ultrasonic transducer, a reflector, a reference reflector and an electronic circuit.

BACKGROUND OF THE INVENTION

U.S. Pat. No. 6,073,491 discloses an arrangement and a method for the contactless distance and pressure measurement within an air spring. Both measurement quantities are determined in accordance with the pulse/echo method with the aid of ultrasonic pulses, which propagate within the air spring flexible member. The distance between the ultrasonic transducer and an end reflector is computed from the running times of the sonic pulses to a first reference reflector and to the end reflector. The static pressure present in the air spring is determined with the aid of a second reference reflector at a defined distance to the first reference reflector. For this purpose, a control unit holds the amplitude of the first echo constant. The damping constant of the air and therefore the pressure is computed from the ratio of the amplitudes of the first and second reference echos.

From theoretical considerations, it results that this pressure-measurement method is not especially sensitive and therefore is rather imprecise. A further disadvantage is the relatively high technical complexity, namely, two reference reflectors and a control unit for the transmitting power are necessary.

SUMMARY OF THE INVENTION

It is an object of the invention to provide a cost-effective and precisely functioning method for measuring the static pressure in an air spring wherein the measured air pressure in the air spring can be used also for pressure corrections in a distance measuring method known per se.

The method of the invention is for determining pressure in the interior space of an air spring of a motor vehicle, the air spring including a cover plate and a roll-off piston. The method includes the steps of: providing an ultrasonic pulse/echo measuring arrangement including: an ultrasonic transducer fixedly mounted on the cover plate; a reference reflector fixedly mounted in the air spring; a target reflector fixedly mounted on the roll-off piston; and, a transmitter/receiver evaluation circuit; providing the ultrasonic transducer with a $\lambda/4$ adaptation layer having an impedance unequal to the geometric mean of the impedance of the ultrasonic transducer and the impedance of the the ambient air of the interior space of the air spring so as to define a mismatch; and, generating a reference signal having a running time and an amplitude and evaluating the running time and the amplitude. The running time as well as the amplitude of the reference signal are evaluated to precisely determine the pressure present in the interior space of the air spring.

The method for pressure measurement within an air spring described hereinafter operates in accordance with the pulse/echo principle with the aid of ultrasonic sound. With the aid of a sonic transducer, ultrasonic sound is propagated in the air spring and is reflected over a known reference path. The running time of the echo as well as the amplitude of the electric echo signal are evaluated and the amplitude of the echo signal is dependent upon the transmission characteristics of the reference path and especially on the transmission of the sound energy between the sonic transducer and the air.

The measuring method is based on the Consideration that the transmission T of sonic energy over the boundary layer between two different media is dependent upon the acoustic impedances of these media:

$$T = 2Z_1/(Z_1 + Z_0). \quad (1)$$

The acoustic impedance Z of a medium is the product of its specific density $\rho$ and the velocity c with which the sound waves propagate:

$$Z = \rho c. \quad (2)$$

Based on the gas law, the pressure p in the air spring determines the density $\rho$ of the air which is enclosed in the volume V (at constant temperature):

$$pV = (\text{const})_1 = (\text{const})_2 \cdot p/\rho => \rho = (\text{const})_3 \cdot p. \quad (3)$$

When the acoustic impedance $Z_0$ of the sonic transducer is significantly greater than the impedance $Z_1$ of the air, an almost linear relationship results from the equations (1) to (3) between the pressure p in the air spring and the transmission factor T, which determines the amplitude of the electric echo signal.

That is, the method of the invention for measuring the pressure in the air spring is based not on the pressure-dependent transmission characteristics of the air but on the fact that the transmission of the sound energy from a converter element to the air is dependent upon the static pressure in the air spring.

The arrangement for carrying out the method of the invention includes a piezoceramic ultrasonic transducer, a reference reflector and an electronic circuit, which can evaluate the running times of the echo as well as its signal amplitudes.

The ultrasonic waves are generated by a piezoceramic transducer element whose acoustic impedance is $10^5$ higher than the impedance of the air at ambient pressure. Because of this crude mismatch, the sound waves within the piezoceramic are, in conventional ultrasonic measuring arrangements, almost completely reflected at the boundary layer to the air and only a fraction of the sonic energy is transmitted to the air. For this reason, ultrasonic transducers for use at ambient pressure have a so-called adaptation layer.

The thickness of the adaptation layer must amount to precisely a quarter of the wavelength in order to achieve an energy adaptation and therefore an optimal signal transmission. Furthermore, the acoustic impedance of the material used must correspond to the geometric mean of the impedances of the air and the piezoceramic. The use of an ultrasonic transducer having an adaptation layer is known for the distance measurement in an air spring. In this connection, reference can be made to German patent publication 198 11 982.

The teaching of the present pressure measurement method is based on the fact that the adaptation layer is deliberately mismatched at ambient pressure. In this way, one obtains an almost linear amplitude/pressure characteristic line which is evaluated in accordance with the invention for determining the pressure.

With the pressure in the air spring, the density of the medium increases and therefore its acoustic impedance so that the transmission factor and therefore the signal intensity of the first reference echo increases with the pressure. The measurement arrangement can be calibrated at ambient pressure in order to determine the pressure from the change of the signal amplitude.

When the acoustic impedance of the adaptation layer is greater by a factor of 10 than the impedance of the air at ambient pressure, an almost linear characteristic line for the amplitude ratio in dependence upon the pressure (FIG. 3) results theoretically.

The difference with respect to the arrangement described in U.S. Pat. No. 6,073,491, which has two reference reflectors, is that the method of the invention needs only one reference reflector which is used not only for pressure measurement but also can be used for a pressure-corrected height measurement. The second reflector is not necessary.

The relationship between pressure and the amplitude ratio is in the present method significantly greater than in the method of U.S. Pat. No. 6,073,491. In this way, the complexity is reduced in the evaluation.

According to a third embodiment, the electronic circuit includes a logarithmic amplifier, which compresses the dynamics of the signal. The electrical output signal of this circuit is inverted and refers to a zero potential of 2.5 V (see FIG. 4). FIG. 4 shows the electric trace of the reference signal at ambient pressure as well as at overpressures of 2 bar, 4 bar, 6 bar, 8 bar and 10 bar. The relative minimum of the signal voltage shifts in dependence upon the pressure (see FIG. 5). This characteristic line runs relatively flat because of the logarithmic characteristics.

BRIEF DESCRIPTION OF THE DRAWINGS

The invention will now be described with reference to the drawings wherein:

FIG. 1 is a longitudinal section view through an air spring equipped with a measuring arrangement;

FIG. 2 is a schematic which shows the individual details, in longitudinal section, of the ultrasonic transducer;

DESCRIPTION OF THE PREFERRED EMBODIMENTS OF THE INVENTION

Figure 3:
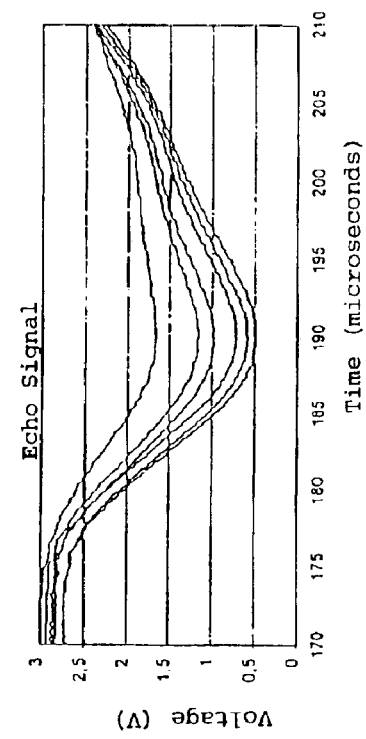
FIG. 3 is the theoretical characteristic line of the pressure measurement as a function of the impedance change.
Figure 4:
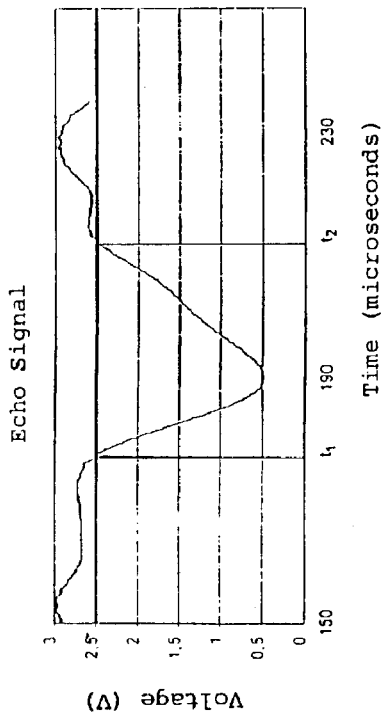
FIG. 4 is a graph showing the electric echo signal at the output of a logarithmic amplifier.
Figure 5:
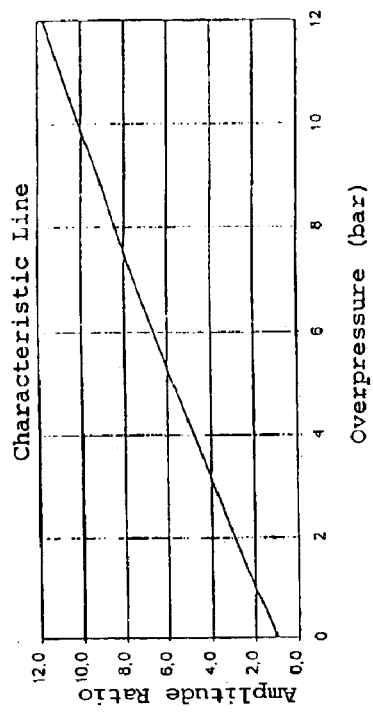
FIG. 5 is a plot of the change of the output voltage as a function of pressure.

The air spring 2 shown in FIG. 1 includes essentially a cover plate 4, a flexible member 6 and a roll-off piston 8. The cover plate 4 is mounted on the chassis and the roll-off piston 8 is mounted at the axle end or wheel end. During the deflection operation, the flexible member 6 rolls on the roll-off piston 8. The clear distance 10 between the clamp plate 16 of the roll-off piston 8 or a bumper 18 and the cover plate 4 is dependent upon the deflection and loading state of the vehicle.

For measuring this distance 10, a piezoceramic ultrasonic transducer 12 is disposed on the cover plate 4 and is configured as a transmitter and receiver.

A reference reflector is mounted at a fixed distance ahead of the ultrasonic transducer 12. The reference reflector 14 can be simply a tensioned wire. The ultrasonic transducer 12 is directed in the direction toward the roll-off piston 8 or, when utilizing a clamp plate 16, the ultrasonic transducer 12 is directed toward the latter. In the present embodiment, a bumper 18 functions as a target reflector and is mounted on the clamp plate 16.

The details relating to the ultrasonic transducer 12 are presented in FIG. 2.

The ultrasonic transducer 12 is provided with an adaptation layer 22 to improve the impedance adaptation to the air of the interior space 20 of the air spring (see FIG. 1). The thickness of this adaptation layer 22 is one fourth of the wavelength of the ultrasonic signal used. The impedance is not, however, as usual, given by the geometric mean of the impedances of the air and of the piezoceramic 12; rather, and according to the invention, the impedance is deliberately selected as a mismatch. Accordingly, a quasi-linear amplitude/pressure characteristic line results which is applied to the determination of the inner pressure of the air spring.

The unit comprised of piezocrystal or piezoceramic 12 and adaptation layer 22 is attached with the aid of a potting compound 24 in a sensor housing 26. This sensor housing has a conical or horn-shaped opening facing in the direction toward the interior space 20 of the air spring. A sheet metal piece is mounted close to the opening and transversely to the longitudinal axis 28 of the beam and functions as reference reflector 14.

Figure 6:
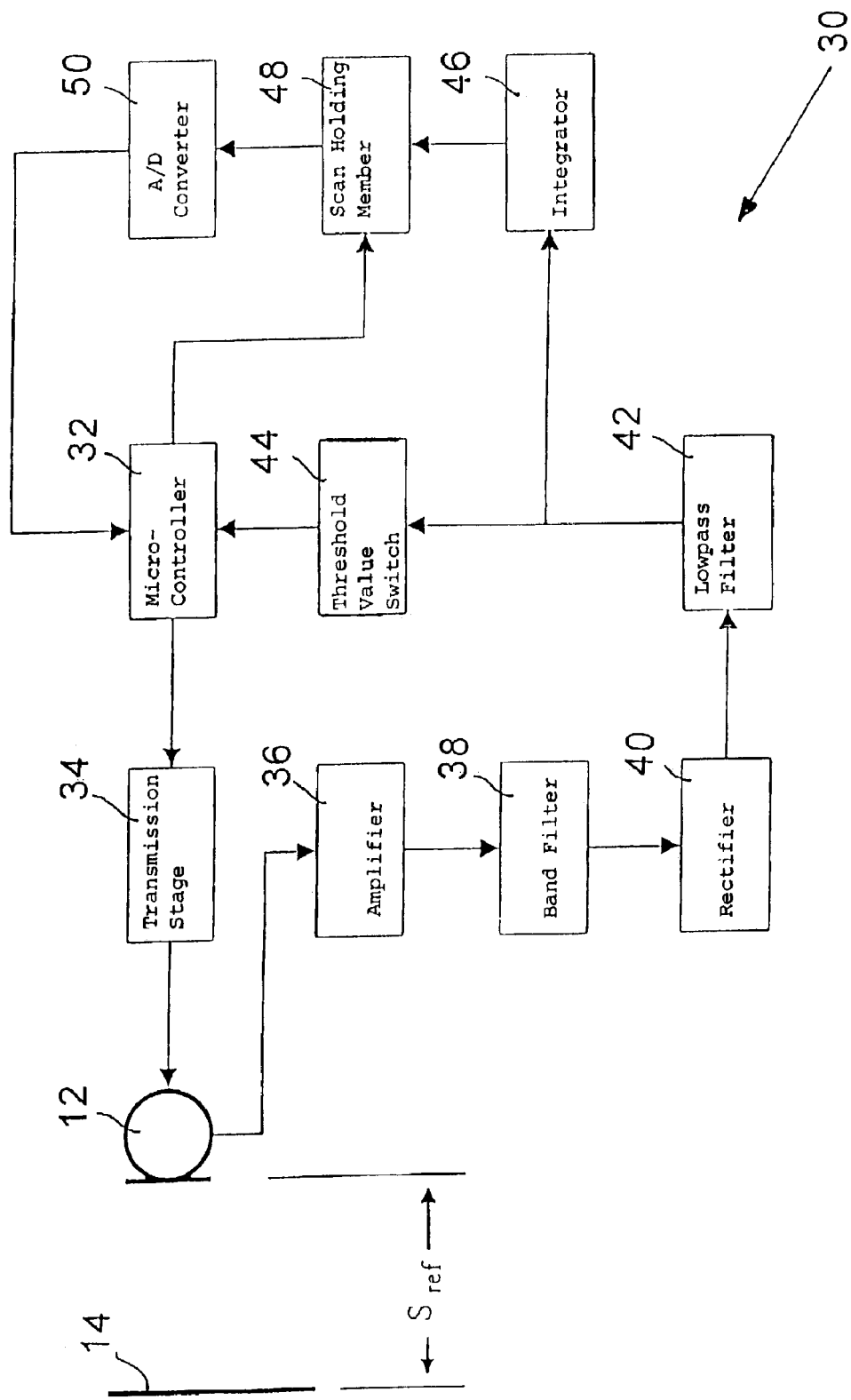
FIG. 6 is a block circuit diagram of the electronic circuit for signal processing.

The signal processing will now be explained with reference to the block circuit diagram shown in FIG. 6 of the transmitter/receiver evaluation electronic circuit 30.

A microcontroller 32 controls the measurements of the echo run time and the amplitude of the echo signal. The controller 32 sets the running time measurement to zero at the start of the measuring cycle. The controller 32 then activates a transmitter stage 34 which first charges the static capacity of the piezoelectric transducer 12 to the required transmitting voltage (5 to 250 Volts) and thereafter suddenly discharges the same. In this way, the piezoceramic 12 is excited to natural oscillations which are transmitted to the air and are reflected at the reference reflector 14 (reference distance $S_{ref}$).

After the natural oscillations have decayed, the sonic transducer 12 can convert the arriving echo into an electric signal based on the reciprocity. The signal voltages which occur amount to several microvolts. The signal is amplified (amplifier 36) and supplied to an active band filter 38, which is matched to the natural frequency of the sonic transducer 12. A rectifier 40 and a downstream lowpass filter 42 extract the envelope from the amplitude-modulated signal. If the amplitude of this echo signal exceeds the adjusted threshold value (threshold value switch 44), the microcontroller 32 interprets this as the time point for the arrival of the echo and stops the measurement of the running time. The microcontroller 32 computes the current or instantaneous propagation velocity of the sound in the air spring 2 from the measured running time and the known length of the reference path $S_{ref}$.

Figure 7:
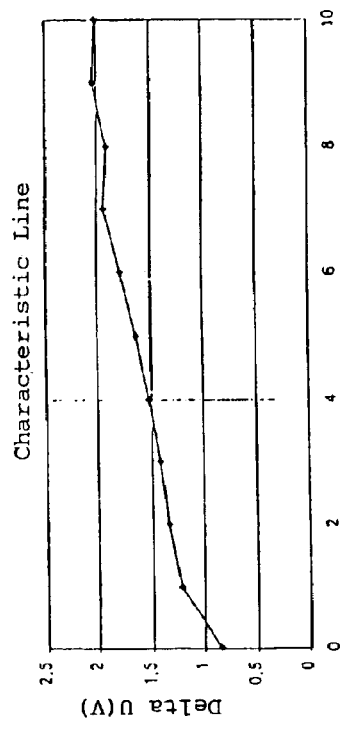
FIG. 7 is a graph showing voltage of the echo signal plotted as a function of time; and, FIG. 8 is a schematic of the circuit for evaluating the amplitude of the reference signal.

To determine the pressure dependency of the signal amplitude, the echo signal (FIG. 7), which is reflected from the reference reflector 14, is supplied to an integrator 46. The voltage-time area of the echo signal is an index for its energy content which is dependent on the pressure, which is to be measured in the air spring, via the transmission factor of the transducer 12.

The microcontroller 32 scans the output signal of the integrator 46 and detects the measurement result via an analog/digital converter 50.

The echo signal shifts in time in dependence upon the temperature. So that the echo signal is always correctly processed, the microcontroller 32 tracks the time points for the start and the end of the integration ($t_1$ and $t_2$). The basis for this is the propagation velocity which the microcontroller had determined in the previous measurements.

Figure 8:
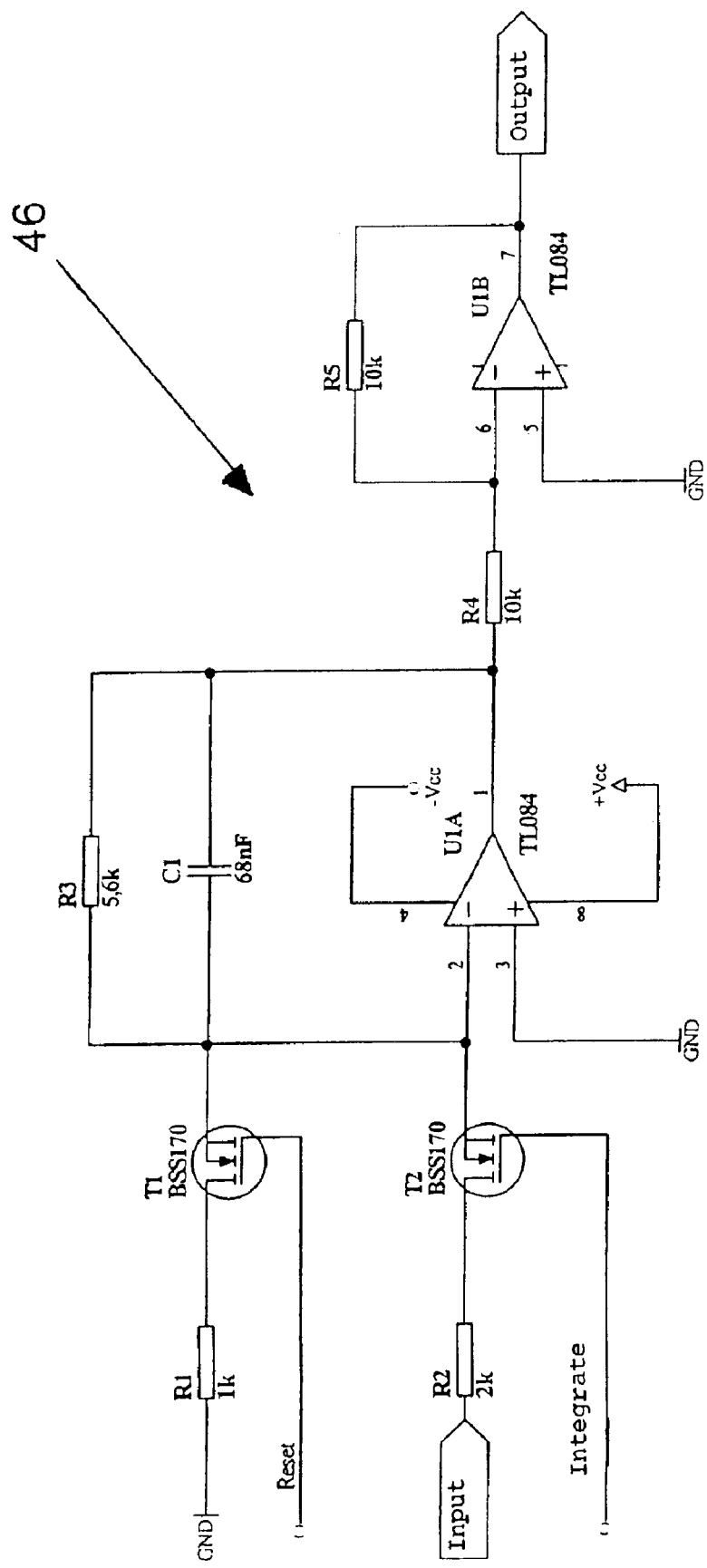

The circuit for evaluating the amplitude of the reference signal is shown in FIG. 8. The circuit here is a controllable integrator 46 which forms the voltage-time area of the reference signal.

The microcontroller 32 determines the start and the end of the integration. In this connection, reference can also be made to FIG. 6.

It is understood that the foregoing description is that of the preferred embodiments of the invention and that various changes and modifications may be made thereto without departing from the spirit and scope of the invention as defined in the appended claims.

What is claimed is:

1. A method for determining pressure in an interior space of an air spring of a motor vehicle, the air spring including a cover plate and a roll-off piston, the method comprising the steps of:

providing an ultrasonic pulse/echo measuring arrangement including: an ultrasonic transducer fixedly mounted on said cover plate; a reference reflector fixedly mounted in said air spring; and, a transmitter/receiver evaluation circuit;

providing said ultrasonic transducer with a $\lambda/4$ adaptation layer having an impedance unequal to the geometric mean of the impedance of the ultrasonic transducer and the impedance of the ambient air of said interior space of said air spring so as to define a mismatch; and, driving said ultrasonic transducer to generate oscillations reflected from said reference reflector and to form a reference signal having a running time and an amplitude; and, evaluating said running time and said amplitude of said reference signal in said transmitter/receiver evaluation circuit to determine said pressure in said interior space of said air spring.

2. The method of claim 1, wherein said evaluation circuit for determining said pressure is calibrated at ambient temperature.

3. The method of claim 1, wherein said ultrasonic transducer have a transmission factor; said evaluation circuit includes an integrator and wherein an echo signal having an energy content is reflected from said reference reflector; and, wherein the method comprises the further step of supplying said echo signal to said integrator to form, as an output signal, a plot of voltage as a function of time defining an area, which is an index for said energy content, which is dependent, via said transmission factor, on the pressure in said air spring to be measured.

4. The method of claim 3, wherein said evaluation circuit includes a microcontroller scanning the output signal of said integrator via a digital/analog converter.

5. An apparatus system for determining pressure in an interior space of an air spring of a motor vehicle, the air spring including a cover plate and a roll-off piston, the apparatus comprising:

an ultrasonic pulse/echo measuring arrangement including: an ultrasonic transducer fixedly mounted on said cover plate; a reference reflector fixedly mounted in said air spring; and, a transmitter/receiver evaluation circuit;

said ultrasonic transducer having a $\lambda/4$ adaptation layer having an impedance unequal to the geometric mean of the impedance of the ultrasonic transducer and the impedance of the ambient air of said interior space of said air spring so as to define a mismatch;

means for driving said ultrasonic transducer to generate a oscillations reflected from said reference reflector and to form a reference signal having a running time and an amplitude; and, said transmitter/receiver evaluation circuit receiving said reference signal to evaluate said running time and said amplitude to determine said pressure in said interior space of said air spring.

6. The apparatus of claim 5, wherein said adaptation layer has an acoustic impedance which is greater than the acoustic impedance of the air in said interior space of said air spring by a factor of ten at ambient pressure.

7. The apparatus of claim 5, wherein said evaluation circuit includes a logarithmic amplifier for compressing the reference signal received by said evaluation circuit.

\* \* \* \* \*